United States Patent
Karhunen et al.

(10) Patent No.: US 10,086,530 B2
(45) Date of Patent: Oct. 2, 2018

(54) PROTECTION OF WOOD

(71) Applicants: Stora Enso Oyj, Helsinki (FI); Tikkurila Oyj, Vantaa (FI); Metsäliitto Osuuskunta, Metsä (FI)

(72) Inventors: Pirkko Karhunen, University of Helsinki (FI); Jorma Matikainen, University of Helsinki (FI); Lasse Kyllönen, University of Helsinki (FI); Pirjo Ahola, University of Helsinki (FI); Ilkka Kilpeläinen, University of Helsinki (FI); Alistair W. T. King, University of Helsinki (FI)

(73) Assignees: Stora Enso Oyj, Helsinki (FI); Tikkurila Oyj, Vantaa (FI); Metsäliitto Osuuskunta, Metsä (FI)

(*) Notice: Subject to any disclaimer, the term of this patent is extended or adjusted under 35 U.S.C. 154(b) by 241 days.

(21) Appl. No.: 14/893,722

(22) PCT Filed: May 26, 2014

(86) PCT No.: PCT/FI2014/050411
§ 371 (c)(1),
(2) Date: Nov. 24, 2015

(87) PCT Pub. No.: WO2014/188080
PCT Pub. Date: Nov. 27, 2014

(65) Prior Publication Data
US 2016/0325459 A1 Nov. 10, 2016
US 2017/0326753 A9 Nov. 16, 2017

(30) Foreign Application Priority Data

May 24, 2013 (FI) .................... 20135568

(51) Int. Cl.
| | |
|---|---|
| B27K 3/34 | (2006.01) |
| A01N 57/16 | (2006.01) |
| C08B 3/20 | (2006.01) |
| C08H 8/00 | (2010.01) |
| C09D 5/14 | (2006.01) |
| C09K 21/12 | (2006.01) |
| C09D 5/18 | (2006.01) |
| C09D 15/00 | (2006.01) |
| C09D 7/40 | (2018.01) |
| C08K 5/5333 | (2006.01) |

(52) U.S. Cl.
CPC .............. *B27K 3/346* (2013.01); *A01N 57/16* (2013.01); *B27K 3/343* (2013.01); *C08B 3/20* (2013.01); *C08H 8/00* (2013.01); *C09D 5/14* (2013.01); *C09D 5/18* (2013.01); *C09D 7/40* (2018.01); *C09D 15/00* (2013.01); *C09K 21/12* (2013.01); *B27K 2240/20* (2013.01); *C08K 5/5333* (2013.01)

(58) Field of Classification Search
CPC .... B27K 3/346; B27K 2240/20; B27K 3/343; A01N 57/16; C08B 3/20; C08H 8/00; C09D 5/14; C09D 5/18; C09D 7/12; C09D 15/00; C09K 21/12; C08K 5/5333
USPC ........................................ 428/537.1
See application file for complete search history.

(56) References Cited

U.S. PATENT DOCUMENTS 3,501,339 A * 3/1970 Gurgiolo .............. B27K 3/0292
427/397
3,906,136 A 9/1975 Weil
(Continued)

FOREIGN PATENT DOCUMENTS

| CN | 1921763 A | 2/2007 |
| CN | 101198254 A | 6/2008 |
(Continued)

OTHER PUBLICATIONS

Finnish Search Report for Patent Application No. 20135568 dated Feb. 6, 2014.
(Continued)

*Primary Examiner* — Leszek Kiliman
(74) *Attorney, Agent, or Firm* — McCormick, Paulding & Huber LLP

(57) ABSTRACT

A method of treating wood with an organic phosphonate salt in a liquid phase to chemically modify its surface and thus provide protection from microorganisms. The organic phosphonate salts are of Formula III

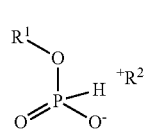

wherein R1 is a hydrogen radical or an alkyl or aryl radical having 1 to 20 carbon atoms and R2 is a cation selected from the group of NH4+, H+, Li+, Na+, K+, Rb+, Cs+, Fr+, Cu+, Ag+, substituted or unsubstituted ammonium, phosphonium, and sulfonium, methylpyrrolidinium, isothiazolium, isoxazolium, oxazolium, pyrrolium, thiophenium, pyridinium, pyridazinium, pyrimidinium, pyrazinium, imidazolium, pyrazolium, thiazolium, oxazolium, 1-ethyl-3-methylimidazolium, and triazolium, or a mixture thereof, said method preferably comprising using one or more salt compounds having formula III. Products comprising a raw material having been treated according to the method with one or more organic salts of formula III are also disclosed.

30 Claims, 2 Drawing Sheets

(56) References Cited

U.S. PATENT DOCUMENTS

| | | | | |
|---|---|---|---|---|
| 4,692,355 | A | * | 9/1987 | Beck .................. B27K 3/08 |
| | | | | 106/18.18 |
| 4,804,384 | A | * | 2/1989 | Rowell ............. B27K 3/346 |
| | | | | 427/212 |
| 4,939,285 | A | | 7/1990 | Weis et al. |
| 6,653,324 | B1 | * | 11/2003 | Kohler ............. B27K 3/343 |
| | | | | 514/315 |
| 2009/0117200 | A1 | * | 5/2009 | Gouot .............. A01N 37/18 |
| | | | | 424/605 |
| 2011/0108782 | A1 | * | 5/2011 | Hansel ............. C09K 21/12 |
| | | | | 252/607 |

FOREIGN PATENT DOCUMENTS

| | | | |
|---|---|---|---|
| GB | 2 257 043 A | | 1/1993 |
| GB | 2257043 | * | 1/1993 |
| JP | 2008540412 A | | 11/2008 |
| JP | 2008546735 A | | 12/2008 |
| RU | 2061589 C1 | | 6/1996 |
| RU | 2075383 C1 | | 3/1997 |
| RU | 2144938 C1 | | 1/2000 |
| RU | 2205750 C2 | | 6/2003 |
| WO | 2011114004 A1 | | 9/2011 |

OTHER PUBLICATIONS

Green, D.W., Evans, J.W., and Craig, B. (2003). Durability of structural lumber products at high temperature. Part 1: 66° C. at 75% RH and 82° C. at 30% RH. Wood and Fiber Science 35(4): 499-523.

* cited by examiner

PROTECTION OF WOOD

CROSS REFERENCE TO RELATED APPLICATIONS

This application is entitled to the benefit of and incorporates by reference subject matter disclosed in International Patent Application No. PCT/FI2014/050411 filed on May 26, 2014 and Finnish Patent Application No. 20135568 filed on May 24, 2013.

TECHNICAL FIELD

The present invention relates to a method of treating wood such as lumber, particle boards, chipboard, hardboard, medium density fibreboard, plywood, laminates, woodchips and other wood-based products.

In such a method, an organic phosphonate salt in liquid phase is applied to a surface of the wood-based product in order to chemically modify said surface and to improve the resistance of the surface to microorganisms and to protect it from weather and fire.

The present invention also relates to wood-based products that have been treated with a wood protection agent in order to improve their resistance to microorganisms, weather and fire and to a wood protection composition.

Further aspects of the invention relate to uses of organic phosphonate salts.

BACKGROUND ART

Wood and wood products have been used throughout history. It is recognised that on exposure to the environment untreated wood undergoes various undesired reactions, e.g. fungi and bacteria can cause oxidation, hydrolysis and reduction of the chemical components of wood and wood products, i.e. degradation of wood surface and cell wall polymers (cellulose, hemicelluloses and lignin), in chemical and enzymatic processes, affecting the properties of the wood.

There are a number of prior art methods for treating wood and wood-based products in order to increase resistance to undesired reactions. These methods typically involve contacting the surface of the wood or wood-based product with an agent comprising toxic or corrosive chemicals, of which there are several commercially available e.g. chromated copper arsenate (CCA), alkaline copper quaternary (ACQ) etc.

These prior art methods have the disadvantages that although they are effective methods for the provision of resistance to undesired reactions, their chemical properties give rise to environmental concerns in the case of e.g. CCA, and are extremely corrosive in the case of e.g. ACQ.

More recent technological advances provide the chemical modification of wood. The most studied of these methods is the reaction of wood with acetic anhydride. Wood contains an abundance of free hydroxyl groups that readily absorb and release water depending on the conditions in which the wood finds itself. When reacted with acetic anhydride the free hydroxyl groups are substituted with acetyl groups (reaction scheme I).

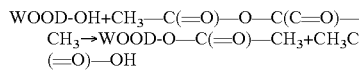

In order to achieve even acetylation the wood must be in a partially swollen state, i.e. moist. This is disadvantageous in that water molecules in the wood will react with acetic anhydride to give acetic acid thus resulting in loss of reagent. Optimum conditions for acetylation are at temperatures in excess of 100° C. as is disclosed in U.S. Pat. No. 4,804,384. It is well known in the art that the mechanical properties of wood suffer as temperature rises, i.e. increasing temperature has a detrimental effect on mechanical properties such as modulus of elasticity, shear modulus, bending strength, tensile strength, compressive strength and shear strength see, e.g. Green et al. 2003.

Further methods are disclosed in which chemical modification is achieved using phosphorus compounds or using sterically hindered amines, e.g. in US patent application 2011/108,782, U.S. Pat. Nos. 4,692,355 and 6,653,324.

SUMMARY

It has been found that the toxicity and environmental threat of traditional wood preservatives through e.g. leaching, as well as the harsh conditions under which chemical modification for the protection of wood surfaces takes place, make the satisfactory provision of wood preservative, wood preservation methods and preserved wood problematic.

It is an aim of the present invention to eliminate at least a part of the problem relating to the prior art and to provide a novel method for improving the resistance of wood and wood products to undesirable reactions.

It is also an aim of the invention to provide a treatment that is capable of chemically modifying the surface of wood in order to improve its resistance to undesirable reactions. It is a further aim to alter the appearance of the surface of the wood so treated wood can be distinguished from untreated wood.

A further aim of the invention is to provide wood products that have been chemically modified in order to increase their resistance to undesirable reactions, and optionally to weather and fire.

The invention is based on the finding that contacting wood with organic phosphonate salts results in a chemical modification of the wood. It would appear that hydroxyl groups present in the wood react with the organic phosphonate salts to give wood phosphonates, reducing potential for leaching of reagents.

A potential reaction scheme II is given in the following, where the phosphonate anion is countered by an organic or inorganic cation:

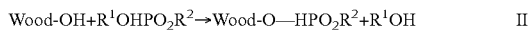

$R^1$ represents H or a hydrocarbyl radical, and
$R^2$ stands for an organic or inorganic cation Surprisingly it has been found that a treatment of this kind, which provides an at least partial phosphonylation of the wood, in particular of the surface thereof, will protect wood from attack by microorganisms and will also prevent its thermal decomposition thus inhibiting the effects of fire. Phosphonylation of the surface also prevents decomposition reactions caused by sunlight.

By means of the method, a product can be formed from a wood raw material having a surface, said surface containing phosphonated groups derived from a chemical reaction between an organic phosphonate salt and hydroxyl groups present in the constituent molecules of the surface of the raw material.

The invention also provides a new composition suitable for treating wood and similar materials such as to increase resistance against undesired reactions caused by microorganisms and increased temperatures. The compositions comprise an aqueous medium and an organic phosphonate salt dissolved or dispersed therein. There are optionally additives and admixtures present in composition. The additives and admixtures include but are not limited to levelling agents and defoamers. The phosphonate salt is present in an amount sufficient to provide protection for the treated surface against said reactions.

More specifically the method according to the present invention is a method of treating wood having a surface, comprising contacting the surface with at least one organic phosphonate salt of Formula III in a liquid phase in order to chemically modify the wood by chemical reaction between the organic phosphonate salt(s) and hydroxyl groups of the wood, wherein the organic phosphonate salts are of Formula III

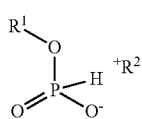

III wherein $R^1$ is a hydrogen radical or an alkyl or aryl radical having 1 to 20 carbon atoms, preferably 3 to 15 carbon atoms, particularly 5 to 12 carbon atoms, advantageously 6 to 10 carbon atoms and $R^2$ is a cation selected from the group of $NH_4^+$, $H^+$, $Li^+$, $Na^+$, $K^+$, $Rb^+$, $Cs^+$, $Fr^+$, $Cu^+$, $Ag^+$, substituted and unsubstituted ammonium, phosphonium, and sulfonium, and five-membered heterocycles having 1, 2 or 3 heteroatoms, including but not limited to methylpyrrolidinium, isothiazolium, isoxazolium, oxazolium, pyrrolium, and thiopheniumpyridinium, pyridazinium, pyrimidinium, pyrazinium, imidazolium, pyrazolium, thiazolium, oxazolium, 1-ethyl-3-methylimidazolium, and triazolium, and mixtures thereof.

The products according to the present invention are such that the raw material is selected from the group consisting of wood and wood products, or a mixture thereof.

The composition is comprising water and at least one organic phosphonate salt of Formula III

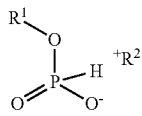

III wherein $R^1$ is a hydrogen radical or an alkyl or aryl radical having 1 to 20 carbon atoms, preferably 3 to 15 carbon atoms, particularly 5 to 12 carbon atoms, advantageously 6 to 10 carbon atoms and $R^2$ is a cation selected from the group of $NH_4^+$, $H^+$, $Li^+$, $Na^+$, $K^+$, $Rb^+$, $Cs^+$, $Fr^+$, $Cu^+$, $Ag^+$, substituted and unsubstituted ammonium, phosphonium, and sulfonium, and five-membered heterocycles having 1, 2 or 3 heteroatoms, including but not limited to methylpyrrolidinium, isothiazolium, isoxazolium, oxazolium, pyrrolium, and thiopheniumpyridinium, pyridazinium, pyrimidinium, pyrazinium, imidazolium, pyrazolium, thiazolium, oxazolium, 1-ethyl-3-methylimidazolium, and triazolium, and mixtures thereof, said composition further comprising a colorant, binder, or combinations thereof.

Novel uses are protecting wood against undesired reactions with microorganisms, protecting wood against fire, and protecting wood against weather.

Considerable benefits are gained with the aid of the present invention. A simple, easy to apply, inexpensive, treatment, applicable under moderate conditions provides protection from microorganisms. The treatment is not leachable by water and thus provides long-term protection from undesirable reactions to the wood to which it is applied without threatening the environment.

Other features and advantages will become apparent from the following description.

BRIEF DESCRIPTION OF THE DRAWINGS

Next preferred embodiments will be examined more closely with the aid of a detailed description and with reference to the attached drawings, in which.

DETAILED DESCRIPTION

Figure 1:
FIG. 1 shows a scanning electron micrograph of untreated wood.
Figure 2:
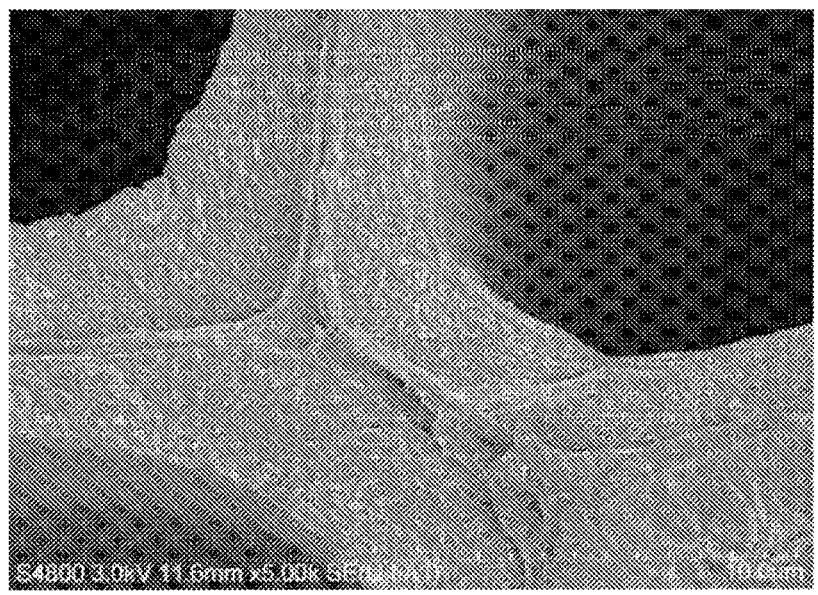
FIG. 2 shows a scanning electron micrograph of treated wood in which the thickness of the fibre wall is doubled.

For the purpose of the present technology, the terms "wood" and "wood products" have broad meanings and are intended to cover a large variety of materials that contain an abundance of hydroxyl groups, e.g. wood, lumber, particle boards, chipboard, hardboard, medium density fibreboard, plywood, laminates or wood chips, or indeed any wood product that has a surface.

As already indicated above, raw-materials comprising or derived from, for example, wood are possible. The wood can be in the form of particles (e.g. sawdust), fibres, granules and chips, shavings etc. having a large range of sizes in the range of typically 0.1 to 100.0 mm (smallest dimension of the particles or part) although these are not absolute limits. The wood may also be in the form of lumber typically used in the construction industry ranging in thickness from 16 mm to 300 mm, in width from 75 mm to 300 mm and in length from 1.8 m to 7.2 m, thus being suitable for any number of applications.

Various sources of wood are covered, both coniferous and deciduous species, including but not limited to spruce, pine, birch, poplar, aspen, alder and eucalyptus.

All of the above materials can be used as such or mechanically or chemically processed, e.g. as medium density fibreboard or plywood.

A method of treating wood with an organic phosphonate salt in a liquid phase to chemically modify its surface and thus provide protection from microorganisms is disclosed. The organic phosphonate salts are of Formula III

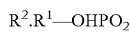

III that equals to

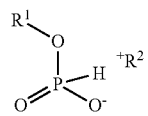

wherein $R^1$ is a hydrogen radical or an alkyl or aryl radical having 1 to 20 carbon atoms, preferably 3 to 15 carbon atoms, particularly 5 to 12 carbon atoms, advantageously 6 to 10 carbon atoms and $R^2$ is a cation selected from the group of $NH_4^+$, $H^+$, $Li^+$, $Na^+$, $K^+$, $Rb^+$, $Cs^+$, $Fr^+$, $Cu^+$, $Ag^+$, substituted or unsubstituted ammonium, phosphonium, and sulfonium, and five-membered heterocycles having 1, 2 or 3 heteroatoms including but not limited to methylpyrrolidinium, isothiazolium, isoxazolium, oxazolium, pyrrolium, thiophenium, pyridinium, pyridazinium, pyrimidinium, pyrazinium, imidazolium, pyrazolium, thiazolium, oxazolium, 1-ethyl-3-methylimidazolium, and triazolium, or a mixture thereof, said method preferably comprising using one or more salt compounds having Formula III. Products comprising a raw material having been treated, according to the method, with one or more organic salts of Formula III are also disclosed.

According to one embodiment the substituent $R^2$ of organic phosphonate salts of Formula III used in the method are selected from $H^+$, $Li^+$, $Na^+$, $K^+$, $Rb^+$, $Cs^+$, $Fr^+$, $Cu^+$, $Ag^+$, substituted or unsubstituted phosphonium, and sulfonium, and five-membered heterocycles having 1, 2 or 3 heteroatoms including but not limited to methylpyrrolidinium, isothiazolium, isoxazolium, oxazolium, pyrrolium, thiophenium, pyridinium, pyridazinium, pyrimidinium, pyrazinium, imidazolium, pyrazolium, thiazolium, oxazolium, 1-ethyl-3-methylimidazolium, and triazolium, or a mixture thereof, said method preferably comprising using one or more salt compounds having Formula III.

According to an exemplary embodiment the substituent $R^2$ of the organic phosphonate salt of Formula III used in the method is selected from methylpyrrolidinium, isothiazolium, isoxazolium, oxazolium, pyrrolium, thiophenium, pyridinium, pyridazinium, pyrimidinium, pyrazinium, imidazolium, pyrazolium, thiazolium, oxazolium, 1-ethyl-3-methylimidazolium, and triazolium. According to a particular embodiment the substituent $R^2$ is 1-ethyl-3-methylimidazolium.

According to a particular embodiment the organic phosphonate salt of Formula III used in the method is 1-ethyl-3-methylimidazolium methylphosphonate ([emim] [MeHPO$_3$]).

As defined herein, to chemically modify the wood is understood by to perform a chemical reaction between at least one organic phosphonate of Formula III and one or more hydroxyl groups of the wood surface.

Various embodiments herein defined describe methods of treating wood that include but are not limited to contacting the surface of the wood with at least one organic phosphonate salt in a liquid phase in order to chemically modify the wood by phosphonylation of the hydroxyl groups of the wood.

For the purpose of the various embodiments the term "liquid phase" has a broad meaning and includes but is not limited to dispersions of the above-mentioned type of organic phosphonate salts in water and other solvents to provide electrolyte solutions. The electrolyte solutions can be translucent or turbid, and may contain a colorant in the form of a dye or a pigment, as well as a binding agent in some embodiments and additional biocides, such as copper azoles like tebuconazole and propiconazole, borates and IPBC (3-iodoprop-2-ynyl N-butylcarbamate). The term "liquid phase" also encompasses neat ionic liquid as well as mixtures of neat ionic liquids. Not leachable by water means that the ionic liquid of the treatment is not removed from the treated wood or wood products or removed only in very minute amounts e.g. at a level not higher than 10 mg/l, preferably 5 mg/l, advantageously 1 mg/l of water percolating through said treated wood and wood products.

As discussed above, contacting wood with organic phosphonate salts in the liquid phase, either as electrolyte solutions or in the form of ionic liquids as concentrated molten salts, or neat ionic liquids, provides protection from microorganisms. The term "electrolyte solution" has a broad definition for the purposes of the present technology and includes but is not limited to an ionic liquid organic phosphonate salt dissolved in a molecular solvent selected from the group of but not limited to water, acetic acid, methanol, ethanol, n-propanol, t-butanol, ammonia, dimethyl sulfoxide, acetonitrile, N,N-dimethylformamide, acetone, ethyl acetate, tetrahydrofuran, dichloromethane, diethyl ether, chloroform, toluene, benzene, cyclohexane, hexane, pentane.

In one embodiment the amount of organic phosphonate salt in the liquid phase is between 0.1 and 100.0%, preferably between 1.0 and 50.0%, advantageously between 2.0 and 20.0% and particularly between 8.0 and 12.0% of the total weight of the liquid phase. In a preferred embodiment the organic phosphonate salts are of Formula III

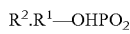

that equals to

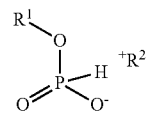

wherein $R^1$ is a hydrogen radical or an alkyl or aryl radical having 1 to 20 carbon atoms, preferably 3 to 15 carbon atoms, particularly 5 to 12 carbon atoms, advantageously 6 to 10 carbon atoms and $R^2$ is a cation selected from the group of $NH_4^+$, $H^+$, $Li^+$, $Na^+$, $K^+$, $Rb^+$, $Cs^+$, $Fr^+$, $Cu^+$, $Ag^+$, substituted and unsubstituted ammonium, phosphonium, and sulfonium, and five-membered heterocycles having 1, 2 and 3 heteroatoms including but not limited to methylpyrrolidinium, isothiazolium, isoxazolium, oxazolium, pyrrolium, thiophenium, pyridinium, pyridazinium, pyrimidinium, pyrazinium, imidazolium, pyrazolium, thiazolium, oxazolium, 1-ethyl-3-methylimidazolium, and triazolium, or a mixture thereof.

In a further embodiment $R^2$ in formula III is an ammonium or phosphonium ion substituted by one or more groups selected from the group of linear or branched alkyl radicals, said alkyl radicals having 1 to 10 carbon atoms, preferably 1 to 8 carbon atoms, advantageously 1 to 5 carbon atoms, most preferably 1 to 4 carbon atoms, or a mixture thereof, or an aryl radical having 4 to 24 carbon atoms, in particular 5 to 18 carbon atoms, said aryl radical optionally comprising at least one heteroatom selected from O, N and S, said alkyl and said aryl radical optionally being substituted with 1 to 10 substituents selected from hydroxyl, carboxy, halo, amino, and thio groups.

In an embodiment the wood is modified by chemical reaction between the organic phosphonate salts and hydroxyl groups of the wood, said chemical reaction giving wood phosphonates and a weight percent gain (WPG) in the wood of 0.001-60.000%, preferably 1.000-55.000%, advantageously 5.000-50.000%, particularly 10.000-40.000%, based on the dry weight of the wood. Such a potentially low amount of organic phosphonate salts provides the benefit of a low-cost treatment for the protection of wood.

In a preferred embodiment, the liquid phase is applied to wood in such a way as to give a coating coverage of 1 m² to 20 m² per liter, preferably 5 m² to 16 m² per liter, advantageously 6 m² to 12 m² per liter of liquid phase, as would be typical for paints, creosotes, varnishes, wood stains, and other coatings, etc.

In a further preferred embodiment the liquid phase is applied at a temperature of 20° C. to 300° C., preferably 35° C. to 270° C., advantageously 45° C. to 230° C., particularly 60° C. to 180° C., ideally 65 to 120° C. and in a yet further embodiment heating occurs during the application or advantageously after the application, or most preferably both during and after application.

Applying the liquid phase at a temperature of at least 20° C. has a beneficial or incremental effect or both on the rate of chemical modification of the wood and indeed on the amount of hydroxyl groups of the wood that are modified. The temperature at which the liquid phase is applied depends on the composition of the liquid phase and the quality of wood to which it is applied.

For the purpose of the present invention, the term phosphonylation is used for designating that at least a part of the functional groups, in particular hydroxyl groups present in the treated specimen, e.g. on the treated surface, are converted into phosphonate groups by the indicated treatment. Typically at least 1% of the available functional groups, which typically are at least partially formed by hydroxyl or phenolic groups, are reacted and optionally converted. In particular at least 5%, in particular about 7 to 100%, for example about 10 to 100% of the hydroxyl groups present in the treated surface, e.g. on the treated surface, are reacted and converted.

The term "protection" and "protected" are used to indicate that the surface or object treated as disclosed herein exhibits an increased resistance against microorganisms, fire or weather, which includes but is not limited to sunlight and moisture, or any combination thereof compared with the corresponding untreated surface. Typically, the resistance of the treated surface will increase with at least 10%, preferably by at least 15%, in particular 20% or more compared with reference, i.e. an untreated specimen.

It would appear, although the present technology should not be limited to this interpretation, that the phosphonate transesterification reaction is accelerated at temperatures in excess of 100° C. (and even up to 200 to 300° C.), for which reason these temperatures require less treatment time. Due care needs to be taken to avoid excessive decomposition of the wood or ionic liquid at those temperatures although some decomposition may be acceptable or even desirable.

Generally, it is preferred to keep decomposition of the treated wood to less than 25%, in particular 0.1 to 20%, calculated as weight loss. Ionic liquid and wood decomposition can be easily measured using thermogravimetric analysis.

Further embodiments allow for application of the liquid phase, in combination with a catalyst or a mixture of catalysts to enhance the reaction and minimise treatment times or temperatures. Typical catalysts include but are not limited to superbases (e.g. N-heterocyclic carbenes, 1,8-diazabicyclo[5.4.0]undec-7-ene (DBU), 1,5-Diazabicyclo[4.3.0]non-5-ene (DBN), 1,1,3,3-tetramethyl-guanidine (TMG), 1,1,2,3,3-pentamethylguanidine (PMG)), Brønsted acid (e.g. hydrochloric acid, sulphuric acid, nitric acid) and Lewis acid catalysts.

Further embodiments provide for methods of application of the liquid phase. In one embodiment the liquid phase is applied with an applicator selected from the group of brush, roller, sponge and spray gun, or a combination thereof.

Typical surface application will allow for penetration of the wood surface to a depth of about 0.1 to 5 mm from the geometrical surface of the specimen. In addition to surface modification, the present technology also provides for treatment of the bulk of the specimens, i.e. below the surface.

In a preferred embodiment the liquid phase is applied by immersing the wood or wood product in it. This embodiment potentially provides for total phosphonylation of the hydroxyl groups of the wood, giving wood phosphonates, thus providing a high degree of protection from the undesired effects of microorganisms.

In a particular embodiment, the liquid phase is applied in a pressure process. The pressure process is carried out in a closed vessel, for example an autoclave, such as a cylinder, with applied pressure (excess pressure or "overpressure"), or under reduced pressure or a combination of both. The pressure process provides a deeper, more uniform penetration of the liquid phase into the wood or wood product, consequently providing a high degree of phosphonylation of the hydroxyl groups, potentially even total phosphonylation of the hydroxyl groups of the wood or wood product and thus a high degree of protection from any combination of the undesired reactions hitherto mentioned.

In a preferred embodiment the vessel is filled with wood or wood product and air is removed from the wood by applying a pressure which is approximately 10-99%, preferably approximately 70-95% lower than normal pressure, for a duration of approximately 10 minutes to 5 hours, preferably approximately 30 minutes to 2 hours, until 70-100%, preferably 75 to 99%, particularly 80 to 98% of the air has been removed from the wood or wood product. The vessel is then filled with the liquid phase until the wood is completely immersed and in an embodiment the pressure is elevated to 1.5-20 bar, preferably 5-15 bar (absolute pressure) for a duration of approximately 1 minute to 24 hours, preferably approximately 10 minutes to 5 hours.

In a further embodiment a pressure of approximately 0.01 to 0.9 bar (absolute pressure), preferably approximately 0.1 to 0.5 bar (absolute pressure) is applied after a treatment in which a pressure higher than normal pressure has been applied for a period of approximately 1 minute to 2 hours, preferably approximately 10 minutes to 1 hour in order to recover excess liquid phase for use in further treatments.

In an alternative particular embodiment the vacuum and pressure processes as described above are carried out at a temperature of approximately 30 to 80° C. degrees, preferably 35 to 70° C.

In an advantageous embodiment the pressure inside the vessel fluctuates between the pressures described in other embodiments and vacuum over a period of approximately 1-10 seconds, preferably 2-5 seconds. This allows for deeper penetration of the liquid phase into the wood or wood product and therefore a higher degree of phosphonylation of hydroxyl groups. The term "fluctuates" in the sense intended here means that the change between the state of overpressure being applied and a state of reduced pressure changes at least once.

Yet further embodiments provide for products. In one embodiment a product is formed from a raw material having a surface, said surface containing phosphonated groups derived from a chemical reaction between an organic phosphonate salt and hydroxyl groups present in the constituent molecules of the raw material.

In a preferred embodiment, a product is provided, for which the raw material is selected from the wood and wood products described in earlier disclosed embodiments, and combinations thereof.

In an advantageous embodiment a product is provided wherein the organic phosphonate salts are selected from those provided in other embodiments, disclosed above, or combinations thereof. In a more preferred embodiment products that are protected from undesired reactions with microorganisms, due to the nature of their chemically modified surfaces are provided.

By means of the present novel technology, the substrate treated will be protected (as defined above) against microorganisms.

Examples of such microorganisms include, but are not limited to viruses, bacteria, fungi, e.g. blue stain fungi, including but not limited to strains of the *Ambrosiella, Aureobasidium, Ceratocystis, Cladosporium* and *Phialophora* families, such as *Aureobasidium pullulans* and *Ceratocystis piceae*, moulds e.g. white-rot mould and brown-rot mould, including but not limited to those strains belonging to the *Cladosporium, Alternaria, Helminthosporium, Penicillium, Aspergillus, Epicoccus* and *Rhizopus* families, protists and metazoa. It also facilitates the collection of excess liquid phase for application to further wood.

In a particular embodiment the surface chemically modified by phosphonate salts provides a product that is protected against sunlight and moisture.

In a more preferential embodiment the surface chemically modified by phosphonate salts provides a product that is protected from fire.

In a still further preferred embodiment, a wood specimen obtained by carrying out any of the above-described methods is provided. In a suitable embodiment, a wood specimen obtainable by any of the above-described methods is provided.

A wood protection composition comprising water, at least one organic phosphonate salt, a colorant, binder, or combinations thereof is provided in a yet further embodiment. In a preferred embodiment the organic phosphonate salts in the composition amount to between 0.1 and 75.0%, preferably between 1.0 and 50.0%, advantageously between 2.0 and 20.0% and particularly between 8.0 and 12.0% of the total weight of the composition.

In a more preferred embodiment the colorant in the wood protection composition is a dye or a pigment or a combination thereof and in a still further preferred embodiment the colorant is selected from the group of cadmium yellow, cadmium red, cadmium green, cadmium orange, carbon black (including vine black, lamp black), ivory black (bone char), chrome yellow and chrome green, cobalt violet, cobalt blue, cerulean blue, aureolin (cobalt yellow), azurite, han purple, han blue, egyptian blue, malachite, paris green, phthalocyanine blue BN, phthalocyanine green G, verdigris, viridian, sanguine, caput mortuum, oxide red, red ochre, Venetian red, Prussian blue, yellow ochre, raw sienna, burnt sienna, raw umber, burnt umber, lead white, cremnitz white, Naples yellow, red lead, vermilion, titanium yellow, titanium beige, titanium white, titanium black, ultramarine, ultramarine green shade, zinc white, zinc ferrite, or a combination thereof.

In an embodiment the colorant is suspended or preferably dissolved in the water of the composition. In a preferred embodiment, the amount of colorant in the composition is between 0.01 and 2.00%, preferably between 0.10 and 1.00%, more preferably between 0.12 and 0.50%, and advantageously between 0.15 and 0.24% of the total volume of the composition.

In one embodiment, the wood protection composition further comprises an additive or an admixture. In a further embodiment the additive is selected from the group consisting of defoamers and levelling agents and mixtures thereof. In a preferred embodiment the admixture is selected from the group of defoamers and levelling agents and mixtures thereof.

In a further embodiment the organic phosphonate salts of the wood protection composition are selected from any of those organic phosphonate salts described in the embodiments above, or a mixture thereof and provide protection against any of the microorganisms hereunto mentioned.

In a further embodiment $R^2$ of the salts of the wood protection composition is an ammonium ion substituted by one or more groups selected from the group of alkyl and aryl groups, said alkyl and aryl groups having 1 to 10 carbon atoms, preferably 1 to 8 carbon atoms, advantageously 2 to 6 carbon atoms, most preferably 3 to 5 carbon atoms, or a mixture thereof.

It is sometimes desirable to augment and supplement the wood preserving properties of the wood protection composition with the addition of a further biocide or biocides. In an embodiment, the biocide or biocides are selected from the group of biocides according to regulation EU528-2012 and their product types PT8 (wood preservatives) and PT6 (in can preservatives). In one embodiment the wood protection composition further comprises an additional biocide selected from the group of copper azoles, borates and 3-iodoprop-2-ynyl N-butylcarbamate and a mixture thereof. In a preferred embodiment the copper azoles of the additional biocide are selected from the group of tebuconazole, propiconzole and a mixture thereof. In a particularly preferred embodiment the borates of the wood protection composition are selected from the group of tetra-n-butylammonium bis[naphthalene-2,3-diolato(2-)-O,O]borate, tetra-n-butylammonium bis[2,2-biphenolato(2-)-O,O]borate, tetra-n-butylammonium bis[3-hydroxy-2-naphthoato(2-)-O, O]borate, tetra-n-butylammonium bis(ortho-hydroxymethylphenolato)borate, tetra-n-butylammonium bis[catecholato (2-)-O,O']borate, tetra-n-butylammonium bis[salicylato(2+ O,O']borate and a mixture thereof. In a suitable embodiment the additional biocide of the wood protection composition is 3-iodoprop-2-ynyl N-butylcarbamate.

In one embodiment a use of organic phosphonate salts for protecting wood against the above-mentioned microorganisms, comprising application of at least one organic phosphonate salt to the wood is disclosed, wherein the organic phosphonate salts are selected from any of the organic phosphonate salts described thus far.

A further embodiment discloses a use of organic phosphonate salts as described above that also provides protection from weather and fire to the wood.

It should be pointed out that the term "surface treatment" used herein should be given a broad interpretation. Thus, for example, it is possible to carry out the invention by modifying wood of small particle size through the bulk of the material, not just the surface, in a relatively mild treatment. Lower particle size allows for better diffusion of the salt through the material.

The following non-limiting working examples illustrate the invention:

EXAMPLES

The examples given below show the degree of growth of various microorganisms on wood samples treated with the phosphonate salts of the present technology as well as the degree of growth of various microorganisms on control and reference samples.

1-ethyl-3-methylimidazolium methylphosphonate ([emim][MeHPO$_3$]) Synthesis

1-Ethylimidazole (96.1 g, 1.00 mol) was added dropwise (over 1 h) to neat dimethylphosphite (110.0 g, 1.00 mol) at 85° C. The reaction was allowed to stir for a further 18 h at 80° C. The mixture was rotary evaporated at 65° C. under high vacuum for 18 h, to yield a clear pale yellow oil (206.0 g, 100%). $^1$H NMR (300 MHz, CDCl$_3$): δ 1.50 (3H, t, J=7.3 Hz), 3.49 (3H, d, J=11.8 Hz), 4.00 (3H, s), 4.29 (2H, q, J=7.3 Hz), 6.85 (1H, d, J=594 Hz), 7.36 (2H, m), 10.69 (1H, s); IR (ATR, cm$^{-1}$) 3146 (CH$_3$), 3048 (CH$_2$), 2943 (CH$_3$), 2300 (PH), 1571 (C=N, C=C), 1460 (CH$_3$), 1231 (CH$_3$), 1178 (MeHPO$_3$), 1047 (MeHPO$_3$).

Wood Treatment

Dry wood chips (11.3 g, spruce) and neat [emim][MeHPO$_3$] (91.8 g) were placed into a flask, flushed with argon, closed and heated in an oven at +50° C. for 48 h. The samples thus obtained were quickly washed with water (3×) and finally immersed in water (500 ml) for 30 min. After drying the weight of the wood sample was 15.3 g, weight increase 36%.

Table 1 shows the degree of growth of white-rot mould on various wood samples over time.

Table 2 shows the degree of growth of blue stain fungi on various wood samples over time.

Table 3 shows the degree of growth of brown-rot mould on various wood samples over time.

TABLE 1

Mould inhibition of the samples (average of three parallel specimens)

| | Mould growth | | | | |
|---|---|---|---|---|---|
| Sample | 1 week | 2 weeks | 3 weeks | 4 weeks | 5 weeks |
| 1 EMIM phosphonate treated spruce specimen 13.9.2010 (small pieces of wood) | — | 0 | 0 | 0 | 0.3 |
| 2 EMIM phosphonate treated (+50° C.) spruce specimen 28.3.2011 | — | 0 | 0 | 0 | 0 |
| 3 Spruce washed with acetone | — | 0 | 1.3 | 1.3 | 1.3 |
| 4 untreated pine wood (reference) | — | 0 | 4.7 | 5 | 5 |

TABLE 2

Blue stain fungi inhibition of the samples (average of three parallel specimens).

| | Blue stain fungi growth | | | | |
|---|---|---|---|---|---|
| Sample | 1 week | 2 weeks | 3 weeks | 4 weeks | 5 weeks |
| 1 EMIM phosphonate treated spruce specimen 13.9.2010 (small pieces of wood) | — | 0.3 | 0.3 | 0.3 | 0.3 |
| 2 EMIM phosphonate treated (+50° C.) spruce specimen 28.3.2011 | — | 2 | 2 | 2 | 2 |
| 3 Spruce washed with acetone | — | 0 | 5* | 5* | 5* |
| 4 untreated pine wood (reference) | — | 4 | 5 | 5 | 5 |

TABLE 3

Decay fungi inhibition of the samples (average of three parallel specimens).

| | Decay fungi growth | | | | |
|---|---|---|---|---|---|
| Sample | 1 week | 2 weeks | 3 weeks | 4 weeks | 5 weeks |
| 1 EMIM phosphonate treated spruce specimen 13.9.2010 (small pieces of wood) | — | 1.3 | 2.7 | 2.7 | 2.7 |
| 2 EMIM phosphonate treated (+50° C.) spruce specimen 28.3.2011 | — | 0.7 | 0.7 | 2.7 | 2.7 |
| 3 Spruce washed with acetone | — | 0 | 5 | 5 | 5 |
| 4 untreated pine wood (reference) | — | 1.7 | 4.7 | 5 | 5 |

* ⅓ contaminated

It was further observed that on exposing treated wood samples to flames ranging in temperature from 200-800° C., the samples failed to ignite.

The present technology is suitable for use in the construction industry, in which it can be used for the protection of lumber and other wood products. Indeed the present technology can be applied in any industry where the protection of lignocellulosic material is called for from shipping to Solutions of the present invention provide a simple, easy to apply, inexpensive, treatment, applicable under moderate conditions to provides protection from microorganisms, protection from fire, protection from sunlight protection from weather and weathering. The treatment is not leachable by water and thus provides long-term protection from undesirable reactions to the wood to which it is applied without threatening the environment or the biosphere.

While the present disclosure has been illustrated and described with respect to a particular embodiment thereof, it should be appreciated by those of ordinary skill in the art that various modifications to this disclosure may be made without departing from the spirit and scope of the present disclosure.

What is claimed is:

1. A method of treating wood having a surface, comprising contacting the surface with at least one organic phosphonate salt of Formula III in a liquid phase in order to chemically modify the wood by chemical reaction between the organic phosphonate salt(s) and hydroxyl groups of the wood, wherein the organic phosphonate salts are of Formula III

wherein R$^1$ is a hydrogen radical or an alkyl or aryl radical having 1 to 20 carbon atoms and R$^2$ is a phosphonium ion substituted by one or more groups selected from the group of linear or branched alkyl radicals, said alkyl radicals having 1 to 10 carbon atoms or a mixture thereof, or an aryl radical having 4 to 24 carbon atoms said aryl radical optionally comprising at least one heteroatom selected from O, N and S, said alkyl and said aryl radical optionally being substituted with 1 to 10 substituents selected from hydroxyl, carboxy, halo, amino, and thio groups.

2. The method according to claim 1, wherein the amount of organic phosphonate salt in the liquid phase is between 0.1 and 100.0% of the total weight of the liquid phase.

3. The method according to claim 1, wherein the wood is modified by chemical reaction between the organic phosphonate salts and hydroxyl groups of the wood, said chemical reaction giving wood phosphonates and a weight percent gain (WPG) in the wood of 0.001-60.000%.

4. The method according to claim 1, wherein the liquid phase is applied to give a coverage of $2m^2$ to $20m^2$ per liter of liquid phase.

5. The method according to claim 1, wherein the liquid phase is applied at a temperature of 20° C. to 300° C., heating occurring during application or after application, or a combination thereof.

6. The method according to claim 1, wherein the liquid phase is applied with an applicator selected from the group of brush, roller, sponge and spray gun, or a combination thereof.

7. The method according to claim 1, wherein the liquid phase is applied by immersing the wood or wood product in it.

8. The method according to claim 1, comprising treating a wood surface on a wood or wood product specimen.

9. The method according to claim 1, wherein the liquid phase is applied in a pressure process that is carried out in a closed vessel at excess pressure, or reduced pressure or a combination of both.

10. The method according to claim 9, which is carried out at a temperature of approximately 30 to 80° C.

11. The method according to claim 9, wherein the pressure inside the vessel fluctuates over a period of approximately 1-10 seconds.

12. A product formed from a raw material having a surface, said surface containing phosphonated groups derived from a chemical reaction between an organic phosphonate salt of Formula III and hydroxyl groups present in the constituent molecules of the surface of the raw material, wherein the organic phosphonate salts are of Formula III

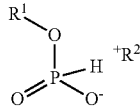

III wherein $R^1$ is a hydrogen radical or an alkyl or aryl radical having 1 to 20 carbon atoms and $R^2$ is a phosphonium ion substituted by one or more groups selected from the group of alkyl and aryl groups, said alkyl and aryl groups having 1 to 10 carbon atoms, or a mixture thereof.

13. The product according to claim 12, wherein the raw material is selected from the group consisting of wood and wood products, or a mixture thereof.

14. The product according to claim 12, wherein the chemically modified surface is protected from undesired reaction with microorganisms, fire, sunlight, moisture or a combination thereof.

15. A wood or wood product specimen obtained by a method according to claim 1.

16. A wood or wood product specimen obtainable by a method according to claim 11.

17. A wood or wood product protection composition comprising water and at least one organic phosphonate salt of Formula III

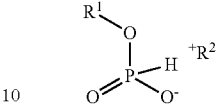

III wherein $R^1$ is a hydrogen radical or an alkyl or aryl radical having 1 to 20 carbon atoms and $R^2$ is a cation selected from the group of $NH_4^+$, $H^+$, $Li^+$, $Na^+$, $K^+$, $Rb^+$, $Cs^+$, $Fr^+$, $Cu^+$, $Ag^+$, substituted and unsubstituted ammonium, phosphonium, and sulfonium, and five-membered heterocycles having 1, 2 or 3 heteroatoms, including but not limited to methylpyrrolidinium, isothiazolium, isoxazolium, oxazolium, pyrrolium, and thiopheniumpyridinium, pyridazinium, pyrimidinium, pyrazinium, imidazolium, pyrazolium, thiazolium, oxazolium, 1-ethyl-3-methylimidazolium, and triazolium, and mixtures thereof, said composition further comprising a colorant, binder, or combinations thereof.

18. The wood protection composition of claim 17, wherein the amount of organic phosphonate salts in the composition is between 0.1 and 75.0% of the total weight of the composition.

19. The wood protection composition according to claim 17, wherein the colorant is a dye or a pigment or a combination thereof selected from the group of cadmium yellow, cadmium red, cadmium green, cadmium orange, carbon black (including vine black, lamp black), ivory black (bone char), chrome yellow and chrome green, cobalt violet, cobalt blue, cerulean blue, aureolin (cobalt yellow), azurite, han purple, han blue, egyptian blue, malachite, paris green, phthalocyanine blue BN, phthalocyanine green G, verdigris, viridian, sanguine, caput mortuum, oxide red, red ochre, Venetian red, Prussian blue, yellow ochre, raw sienna, burnt sienna, raw umber, burnt umber, lead white, cremnitz white, Naples yellow, red lead, vermilion, titanium yellow, titanium beige, titanium white, titanium black, ultramarine, ultramarine green shade, zinc white, zinc ferrite, or a combination thereof and is suspended in the water or is dissolved in the water.

20. The wood protection composition of claim 17, wherein the amount of the colorant in the composition is between 0.01 and 2.00% of the total volume of the composition.

21. The wood protection composition of claim 17, wherein the protection is provided against microorganisms selected from the group consisting of viruses, bacteria, fungi, moulds, protists and metazoa, or a mixture thereof.

22. The wood protection composition of claim 17, wherein $R^2$ is an ammonium ion substituted by one or more groups selected from the group of alkyl and aryl groups, said alkyl and aryl groups having 1 to 10 carbon atoms, or a mixture thereof.

23. The wood protection composition of claim 17, further comprising an additive or an admixture.

24. The wood protection composition of claim 23, wherein the additive is selected from the group of defoamers and levelling agents and a mixture thereof.

25. The wood protection composition of claim 23, wherein the admixture is selected from the group of defoamers and levelling agents and a mixture thereof.

26. The wood protection composition of claim 17, further comprising an additional biocide selected from the group of copper azoles, borates and 3-iodoprop-2-ynyl N-butylcarbamate, biocides according to regulation EU528-2012 and their product types PT8 (wood preservatives) and PT6 (in can preservatives), and a mixture thereof.

27. The wood protection composition of claim 26, wherein the copper azoles are selected from the group of tebuconazole and propiconzole and a mixture thereof.

28. The wood protection composition of claim 26, wherein the borates are selected from the group of tetra-n-butylammonium bis[naphthalene-2,3-diolato(2)-O,O]borate, tetra-n-butylammonium bis[2,2-biphenolato(2-)-O,O]borate, tetra-n-butylammonium bis[3-hydroxy-2-naphthoato (2-)-O,O]borate, tetra-n-butylammonium bis(ortho-hydroxymethylphenolato)borate, tetra-n-butylammonium bis[catecholato(2-)-O,O']borate, tetra-n-butylammonium bis[salicylato(2-)-O,O']borate and a mixture thereof.

29. The wood protection composition of claim 26, wherein the additional biocide is 3-iodoprop-2-ynyl N-butylcarbamate.

30. Use of organic phosphonate salts for protecting wood against undesired reactions with microorganisms, comprising application on a surface of the wood at least one organic phosphonate salt in a liquid phase, wherein the organic phosphonate salts are of formula III

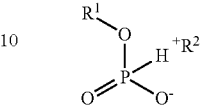

III wherein $R^1$ is a hydrogen radical or an alkyl or aryl radical having 1 to 20 carbon atoms and $R^2$ is a phosphonium ion substituted by one or more groups selected from the group of alkyl and aryl groups, said alkyl and aryl groups having 1 to 10 carbon atoms, or a mixture thereof.

* * * * *

UNITED STATES PATENT AND TRADEMARK OFFICE
CERTIFICATE OF CORRECTION

PATENT NO. : 10,086,530 B2
APPLICATION NO. : 14/893722
DATED : October 2, 2018
INVENTOR(S) : Pirkko Karhunen et al.

It is certified that error appears in the above-identified patent and that said Letters Patent is hereby corrected as shown below:

In the Claims

Column 15, Claim 28, Line 12, "butylammonium bis[naphthalene-2,3-diolato(2)-O,O]borate" should read as:
"butylammonium bis[naphthalene-2,3-diolato(2-)-O,O]borate"

Signed and Sealed this
Fifth Day of March, 2019

Andrei Iancu
*Director of the United States Patent and Trademark Office*